(12) United States Patent
Sherwood

(10) Patent No.: US 6,500,313 B2
(45) Date of Patent: Dec. 31, 2002

(54) METHOD FOR PRODUCTION OF HYDROCARBONS

(76) Inventor: Steven P. Sherwood, 10182 Foxridge Cir., Highlands Ranch, CO (US) 80126

( * ) Notice: Subject to any disclaimer, the term of this patent is extended or adjusted under 35 U.S.C. 154(b) by 0 days.

(21) Appl. No.: 09/837,000

(22) Filed: Apr. 17, 2001

(65) Prior Publication Data

US 2002/0175067 A1 Nov. 28, 2002

Related U.S. Application Data

(60) Provisional application No. 60/257,265, filed on Dec. 19, 2000.

(51) Int. Cl.[7] ................................................. C07C 1/00
(52) U.S. Cl. .................................................. 204/157.15
(58) Field of Search ..................................... 204/157.15

(56) References Cited

U.S. PATENT DOCUMENTS

| | | | |
|---|---|---|---|
| 1,656,813 A | 1/1928 | Bird ........................... 585/416 |
| 1,677,363 A | 7/1928 | Olivier ....................... 585/500 |
| 1,958,648 A | 5/1934 | Steigerwald et al. ........ 260/168 |
| 1,986,238 A | 1/1935 | Winkler et al. .............. 260/168 |
| 2,028,014 A | 1/1936 | Reinecke ..................... 204/31 |
| 2,061,598 A | 11/1936 | Smith et al. ................ 260/170 |
| 4,444,984 A | 4/1984 | Jones et al. ................. 585/500 |
| 4,695,663 A | 9/1987 | Hall et al. ................... 585/417 |
| 4,704,488 A | 11/1987 | Devries et al. ............. 585/415 |
| 4,705,908 A | 11/1987 | Gondouin ................... 585/500 |
| 4,721,828 A | 1/1988 | Withers ....................... 585/500 |
| 4,769,508 A | 9/1988 | Gastinger et al. ........... 585/500 |
| 4,788,372 A | 11/1988 | Gaffney ....................... 585/500 |
| 4,795,849 A | 1/1989 | Gaffney et al. ............. 585/500 |
| 4,827,071 A | 5/1989 | Hazbun ....................... 585/443 |
| 4,864,073 A | 9/1989 | Han et al. ................... 585/943 |
| 4,973,776 A | 11/1990 | Allenger et al. ............. 585/310 |
| 5,053,575 A | 10/1991 | Nikravech et al. .......... 585/500 |
| 5,198,596 A | 3/1993 | Kaminsky et al. .......... 585/500 |
| 5,214,226 A | 5/1993 | Bauer et al. ................. 585/658 |
| 5,328,575 A | * 7/1994 | Geiger ................... 204/157.15 |
| 5,414,176 A | 5/1995 | Amariglio et al. .......... 585/500 |
| 6,077,492 A | * 6/2000 | Anpo et al. ................. 423/239.1 |

OTHER PUBLICATIONS

Mleczko et al., "Catalytic Oxidative Coupling of Methane–Reaction Engineering Aspects and Process Schemes", Fuel Processing Technology, vol. 42, pp. 217–248. (no month available) 1995.*

Erarslanoglu et al., "Oxidative Coupling of Methane on Superconductor–Type Catalytic Materials", Chem. Eng. Comm., vol. 135, pp. 71–79. (no month available) 1995.*

Pugsley et al., "The Circulating Fluidized Bed Catalytic Reactor: Reactor Model Validation and Simulation of the Oxidative Coupling of Methane", Chem. Engin. Sci., vol. 51, No. 11, pp. 2751–2756. (no month available) 1996.*

Do et al., "The Catalytic Oxidative Coupling of Methane: I. Comparison of Experimental Performance Data from Various Types of Reactor", The Canadian J. Chem. Engin., vol. 73, pp. 327–336. Jun. 1995.*

Ogura et al., "Photochemical Conversion of Methane", J. of Molecular Catalysis, vol. 43, pp. 371–379. (no month available) 1988.*

Okabe et al., "Vacuum Ultraviolet Photolysis of Ethane: Molecular Detachment of Hydrogen", J. of Chem. Phys., vol. 34, No. 2, pp. 668–669. Feb. 1960.*

(List continued on next page.)

Primary Examiner—Edna Wong
(74) Attorney, Agent, or Firm—Sheridan Ross P.C.

(57) ABSTRACT

A method for converting methane, ethane, and propane into higher molecular weight hydrocarbons and coproduct hydrogen wherein a molecular oxidant-free gas comprising methane, ethane, and/or propane is exposed to ultraviolet light. Through an oxidative coupling mechanism, the feed gases are converted to free radicals which combine to form higher molecular weight hydrocarbons.

2 Claims, 1 Drawing Sheet

OTHER PUBLICATIONS

Ausloos et al., "Direct and Inert–Gas–Sensitized Radiolysis and Photolysis of Methane in the Solid Phase", J. of Chem. Phys., vol. 42, No. 2, pp. 540–548. Jan. 1964.*
Ausloos et al., "Radiolysis of Methane", J. of Chem. Phys., vol. 38, No. 9, pp. 2207–2214. May 1963.*
Ausloos et al., "Effect of Pressure in a Radiolysis and Photolysis of Methane", J. of Chem. Phys., vol. 40, No. 7, pp. 1854–160. Apr. 1964.*
Mahan et al., "Vacuum Ultraviolet Photolysis of Methane", J. of Chem. Phys., vol. 37, No. 2., pp. 207–211. Jul. 1962.*
Leighton et al., "Photochemical Decomposition of Methane", J. of Amer. Chem. Soc., Communications to the Ed., p. 1823. (no month available) 1936.*
Mordaunt et al., "Primary Product Channels in the Photodissociation of Methane at 121.6nm", J. Chem. Phys., vol. 98, No. 3, pp. 2054–20–65. Feb. 1993.*
Wu et al., "Site Specificity in Molecular Hydrogen Elimination From Photodissociation of Propane at 157 nm", Communications, vol. 111, No. 5, pp. 1793–1796. (no month available) 1999.*
Heck et al., "Photofragment Imaging of Methane", J. Chem. Phys., vol. 104, No. 11, pp. 4019–4030. Mar. 1996.*
Irle et al., "A Molecular Orbital Study on H and H2 Elimination Pathways From Methane, Ethane, and Propane", J. Chem Phys., vol. 113, No. 15, pp. 6139–6148. Oct. 2000.*
Ellis et al., The Chemical Action of Ultraviolet Rays, Chapter 22, pp. 393–395. (no month availabel) 1941.*
*References U–X were incompletely cited on Applicants' Information Disclosure Statement (paper No. 2).*
Irle et al., 2000, J. Chem. Phys., 113(15):6139–6148, No month available.
Heck et al., 1996, J. Chem. Phys., 104(11):4019–4030, No month available.
Wu et al., 1999, Communications, 0021–9606/99/ 111(5):1793–1796, No month available.
Mordaunt et al., J. Chem. Phys., 98(3):2054–2065 Feb. 1993.
Okabe, in Photochemistry of Small Molecules, John Wiley & Sons, New York, pp. 298–299 No month available.
Ellis et al., in Chemical Action of Ultraviolet Rays, Chapter 22, F. Heyroth, ed., Reinhold Publishing Corporation, New York, 1941, pp. 393–395, No month available.
Noyes, Jr. et al., The Photochemistry of Gases, F. Heyroth, ed., Reinhold Publishing Corporation, New York, 1941, pp. 330–331+ Appendices.
Leighton et al., Sep. 1936, J. Am. Chem. Soc., Communications to the Ed., p. 1823, No month available.
Mahan et al., 1962, J. Chem. Phys., 37(2):207–211, No month available.
Ausloss et al., 1963, J. Chem. Phys., 38(9):2207–2214, No month available.
Ausloos, 1964, J. Chem. Phys., 40(7):1854–1860, No month available.
Ausloos et al., 1964, J. Chem. Phys., 42(2):540–548, No month available.
Okabe et al., 1960, J. Chem. Phys., 34(2)668–669, No month available.
Barltrop et al., in Excited States in Organic Chemistry, John Wiley & Sons, London, p. 335 No date available.
Calvert et al., Photochemistry of the Polyatomic Molecules, 492–579 No date available.
Ogura et al., 1988, Journal of Molecular Catalysis, 43, 371–379, No month available.
Do et al., 1995, The Canadian Journal of Chemical Engineering, 73, 327–336, No month available.
Pugsley et al., Chemical Engineering Science, 1996, 51(11), 2751–2756, No month available.
Erarslanoglu et al., Chemical Engineering Comm., 1995, 135, 71–79, No month available.
Mleczko et al., Fuel Processing Technology, 1995, 42, 217–248, No month available.

* cited by examiner

METHOD FOR PRODUCTION OF HYDROCARBONS

This application claims the benefit of Provisional Patent Application Serial No. 60/257,265 filed in the U.S. Patent and Trademark Office on Dec. 19, 2000.

FIELD OF THE INVENTION

The present invention relates to a process for producing liquids containing hydrocarbons of a higher molecular weight than methane from a hydrocarbon feedstock containing a major proportion of methane.

BACKGROUND OF THE INVENTION

Gas-to-liquid conversion technologies use chemical means to convert methane or natural gas to a liquid form suitable for ready transport or direct use. This conversion is accomplished by altering the composition of the hydrocarbon gas molecules to form stable liquids that can be used directly as a chemical feedstock or transportation fuel. There are two known approaches to accomplish this conversion; partial oxidation and oxidative coupling. In the partial oxidation process, hydrocarbons, oxygen and/or water are converted to a synthetic gas containing molecular hydrogen and carbon monoxide. These constituents are recombined in a second process to produce paraffins and high molecular weight fuels such as diesel fuel and heating oil. In the oxidative coupling reaction, hydrocarbon gases are directly converted into desirable liquid hydrocarbons through a series of free radical addition mechanisms.

Known oxidative coupling technologies use oxygen to convert methane to the methyl free radical and water in the presence of a catalyst at temperatures of 800 to 1000° C. The major challenge of these technologies is the rapid conversion of the radicals to carbon dioxide before the radicals can link-up, greatly limiting the conversion to higher molecular weight compounds.

Previous synthetic routes to producing higher molecular weight hydrocarbons from lower molecular weight hydrocarbons have started from feedstocks which have at least two carbon atoms. Such feedstocks are initially dimerised or oligomerised at temperatures in the region of 500–600° C. Such processes are described, for example, in U.S. Pat. Nos. 1,677,363; 4,721,828; 4,769,828; and 5,414,176.

DETAILED DESCRIPTION OF THE INVENTION

Figure 1:
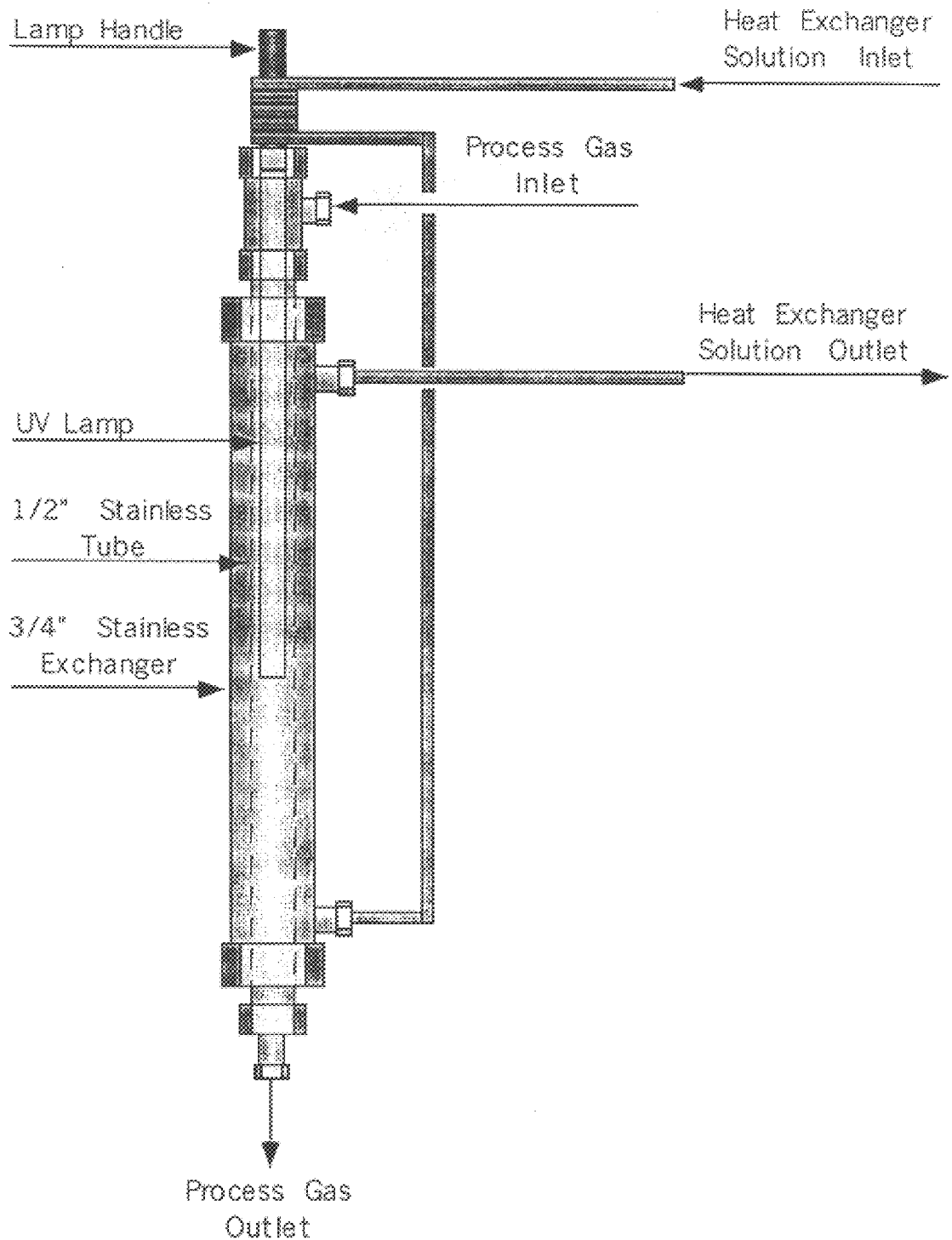
FIG. 1 shows a schematic of the tube reactor that may be used in one embodiment of the present invention.

The present invention provides an coupling process which does not require oxygen or any other oxidant thereby eliminating the conversion of methane to carbon dioxide. In this new process, methane is converted to a methyl radical and a hydrogen radical by exposing the gas to ultraviolet radiation. The formation of these free radicals is confirmed by the presence of ethane and $H_2$ in the reaction product gas. These molecules are produced when two methyl radicals combine to produce ethane and two hydrogen radicals combine to form $H_2$.

It has now been found that higher molecular weight hydrocarbons can be produced from lower molecular weight hydrocarbon feedstocks, and particularly those containing predominately less than three carbon atoms in the presence of ultra violet radiation, a photocatalyst (optionally), and in the absence of molecular oxidants. Accordingly, the present invention provides a process for producing liquids containing hydrocarbons of a higher molecular weight than methane comprising bringing into contact in the vapor phase a hydrocarbon feedstock, such as one containing a major proportion of methane, and optionally, a photocatalyst composition in the presence of ultraviolet radiation and in the absence of molecular oxidants.

The hydrocarbon feedstock can have at least 50% w/w, preferably at least 70% w/w of methane, more preferably at least 90% w/w and may be admixed with other molecular weight hydrocarbons such as ethane or propane. The additional hydrocarbon in the feedstock, if any, may include ethane, ethylene, propane, propylene or mixtures thereof. The feedstock may contain in addition, other open chain hydrocarbons containing between 3 and 8 carbon atoms as coreactants. Specific examples of such additional coreactants are propane, propylene, n-butane, isobutane, n-butenes and isobutene. Suitable feedstock gas may include methane, natural gas, off gas from decomposing biomass, methane from coal mines, and waste methane gas from chemical processes.

The hydrocarbon feedstock is thereafter contacted in the vapor phase with light in wavelength regions of about 150 nm to about 280 nm, i.e., ultra-violet radiation, and in the absence of molecular oxidants. The reaction is preferably conducted at a temperature between about 0° C. and about 800° C., preferably above about 60° C. The reaction is preferably conducted in an inert atmosphere. The inert atmosphere may be provided by a gas inert under the reaction conditions such as nitrogen. In fact, once the reactor has been initially flushed with an inert gas such as nitrogen to remove any oxygen or oxidising gases, there is no need to add further amounts of the inert gas to the reaction system. Any unreacted hydrocarbon feedstock and by-products recovered from the reaction products may be recycled to the reaction.

Photocatalytic reactions using the titanium oxide catalyst have been the focus of research as an environmentally-friendly and safe means of converting light energy into useful chemical energy at ordinary temperatures without generating any pollutants. Other photocatalysts, such as platinum, can be used as well. Photocatalytic reactions proceed when the reaction systems are irradiated with ultraviolet-light in wavelength regions shorter than about 380 nm necessitating the use of an ultraviolet light source. Preferably, the ultraviolet radiation is provided at a wavelength of about 150 nm to about 280 nm.

The feedstock gas may be maintained at an increased pressure to increase molecular interactions with the gas and thereby decrease the necessary reaction time. Although the reaction will proceed within a feedstock gas maintained as less than atmospheric pressures, preferably the feedstock gas is maintained at a pressure greater than about 4psig during the exposure to the ultraviolet radiation.

The reaction may occur in any reaction vessel which provides sufficient contact between the ultraviolet light and the feedstock gas and in the absence of molecular oxidants. In one embodiment, the reaction is conducted in a tube reactor into which the light source has been fitted in the annular space. The reactor has an inlet and outlet valve and a jacket providing for the exchange of a temperature controlling liquid. The ultraviolet lamp may be a standard Pen-Ray lamp (UVP Products) fitted with a fused quartz envelop which does not allow for the transmittance of the vacuum UV (minus 200 nm) mercury spectral emission, or a UV lamp fitted with a special quartz envelop which permits transmittance of the ultraviolet light. Preferably, the source of ultraviolet radiation permits more than 80% transmittance of the vacuum ultraviolet light.

The level of oxygen in the present process is maintained as low as possible to reduce the production of oxygenated products that ultimately interfere with the radical reaction thereby decreasing performance. Preferably, oxygen is maintained at a level of less than about 5%, more preferably less than about 3%, and most preferably less than about 1% in the reaction feedstock.

The higher molecular weight hydrocarbons are recovered by condensing the products to a liquid in an air or liquid chilled cooling vessel. Hydrogen gas is recovered with a hydrogen specific membrane.

EXAMPLES

A series of batch studies were conducted to examine efficiencies of two types of ultraviolet lamp for the conversion of methane to hydrogen and higher molecular weight hydrocarbons. One UV source investigated was a standard Pen-Ray lamp (UVP Products Cat. No. 90-0004-01). This lamp was fitted with a fused quartz envelop which does not allow for the transmittance of the vacuum UV (minus 200 nm) mercury spectral emission. The second UV lamp was fitted with a special quartz envelop which permitted more than 80% transmittance of the vacuum UV light.

In these tests, the selected UV lamp source was placed in the annular space of a ½-inch diameter stainless steel jacketed tube reactor. A schematic of the tube reactor is provided in FIG. 1. A cooling or heated solution was recirculated through the heat exchanger jacket to maintain targeted temperatures. During these tests the reactor was charged with 30 psig methane (CP Grade) and the stagnant gas exposed to UV light for 18 hours. At the conclusion of each test, the product gas was analyzed by hydrogen content (GC analysis). Results from these studies are summarized in the following table.

| | Batch 18 Hour UV/Temperature Study | |
| --- | --- | --- |
| | Mole Percent Hydrogen in Reaction Gas Mixture | |
| Reaction Temperature, °C. | Standard Quartz Envelop Lamp (Minimal Vacuum UV) | Special Quartz Envelop Lamp (80% Transmittance of Vacuum UV) |
| 10 | 0.069 | Not Tested |
| 15 | 0.097 | Not Tested |
| 20 | 0.240 | 0.911 |
| 30 | 0.368 | Not Tested |
| 40 | 0.635 | Not Tested |
| 50 | Not Tested | 0.319 |
| 60 | 0.310 | 3.9 |
| 60 (Rerun) | Not Tested | 4.03 |

These results show that highest hydrogen production was achieved when methane was exposed to vacumm UV (minus 200 nm) radiation at a reaction temperature of 60° C.

Effect of Long Exposure Time and Air (Oxygen) on Vacuum UV Process

To determine the long-term effectiveness of the special quartz process, the tube reactor was charged with 10 psig methane (CP grade) and the gas exposed to UV radiation at a controlled temperature of 60° C. After eight days of UV exposure, a sample of process gas was taken for analysis and the reaction mixture spiked with a small amount of air, and the process gas resampled three and four days later. Results from these tests are provided in the following table.

| | Mole Percent in Product Gas | | |
| --- | --- | --- | --- |
| Analyte | 8-Day UV Exposure -No Air | Third Day After Air Spike | Fourth Day After Air Spike |
| Hydrogen | 32 | 25 | 25 |
| Methane | 59 | 57 | 53 |
| Carbon Dioxide | 0.25 | 3.3 | 3.9 |
| GC/MS Analysis | Higher Molecular Weight Hydrocabons from C2 to C12 in Product Gas | | |

After eight days of exposure to vacuum UV radiation, approximately 40 mole percent of the initial methane charge was converted to hydrogen and higher molecular weight hydrocarbons. Hydrocarbons containing up to 12 carbons were found in the product gas mixture. The introduction of a small amount of air consumed hydrogen and increased the carbon dioxide levels in the product gas. The air spike also reduced the rate of methane conversion from approximately 5% per day to less than 2% per day.

What is claimed is:

1. A method of producing hydrocarbon material, comprising:

exposing a feedstock comprising methane in vapor phase maintained at a temperature greater than about 400° C. to ultraviolet radiation having a wavelength in the range of about 150nm to about 280 nm, in the absence of a molecular oxidant to produce higher molecular weight hydrocarbons; and recovering a hydrocarbon material having a higher molecular weight than said methane.

2. A method of producing hydrocarbon material, comprising;

exposing a feedstock comprising methane in vapor phase maintained at a pressure of greater than about 4 psig to ultraviolet radiation having a wavelength in the range of about 150 nm to about 280 nm, in the absence of a molecular oxidant to produce higher molecular weight hydrocarbons; and recovering a hydrocarbon material having a higher molecular weight than said methane.

* * * * *